United States Patent [19]

van Wijngaarden et al.

[11] Patent Number: 4,869,837
[45] Date of Patent: Sep. 26, 1989

[54] PREPARATION OF A BASIC SALT

[75] Inventors: Gerhard d. van Wijngaarden; Henricus M. J. Brons, both of Amsterdam, Netherlands

[73] Assignee: Shell Oil Company, Houston, Tex.

[21] Appl. No.: 212,389

[22] Filed: Jun. 27, 1988

[30] Foreign Application Priority Data

Jul. 9, 1987 [GB] United Kingdom ............... 8716159

[51] Int. Cl.$^4$ .......................................... C10M 105/22
[52] U.S. Cl. ......................................... 252/39; 252/38
[58] Field of Search ................... 252/38, 39; 549/233

[56] References Cited

U.S. PATENT DOCUMENTS

| | | | |
|---|---|---|---|
| 3,055,829 | 9/1962 | Wiley et al. | 252/18 |
| 3,172,892 | 3/1965 | Le Suer et al. | 260/326.5 |
| 3,219,666 | 11/1965 | Norman et al. | 260/268 |
| 3,231,587 | 1/1966 | Rense | 260/346.8 |
| 3,271,310 | 9/1966 | Le Suer | 252/39 |
| 3,567,637 | 3/1971 | Sabol | 252/39 |
| 3,714,042 | 1/1973 | Greenough | 252/33.2 |
| 3,912,764 | 10/1975 | Palmer | 260/346.8 |
| 4,539,126 | 9/1985 | Bleeker | 252/39 |
| 4,647,387 | 3/1987 | Muir | 252/25 |

FOREIGN PATENT DOCUMENTS

| | | | |
|---|---|---|---|
| 0208750 | 10/1956 | Australia | 252/39 |
| 248465 | 12/1987 | European Pat. Off. | |
| 1053124 | 3/1956 | Fed. Rep. of Germany | 252/39 |
| 786167 | 11/1957 | United Kingdom | |
| 818325 | 8/1959 | United Kingdom | |
| 1289003 | 9/1972 | United Kingdom | |
| 1290251 | 9/1972 | United Kingdom | |
| 1483729 | 8/1977 | United Kingdom | |
| 2097417 | 11/1982 | United Kingdom | |

*Primary Examiner*—William R. Dixon, Jr.
*Assistant Examiner*—James M. Hunter, Jr.

[57] ABSTRACT

Process for the preparation of a basic alkaline earth metal salt of a blend of organic carboxylic acids, which comprises (a) preparing a mixture of one equivalent of the blend of organic carboxylic acids and more than one equivalent of an alkaline earth metal hydroxide and/or oxide in a hydrocarbon solvent;

(b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises an oil-soluble alkyl salicylic acid and one or more hydrocarbon substituted succinic acids or anhydrides, in which the hydrocarbon radical has a number average molecular weight from 120 to 5000.

19 Claims, No Drawings

PREPARATION OF A BASIC SALT

FIELD OF THE INVENTION

The present invention relates to a process for the preparation of a basic alkaline earth metal salt of a blend of organic carboxylic acids, a salt thus prepared and to oil compositions containing such a salt.

BACKGROUND OF THE INVENTION

The use of alkaline earth metal salts of organic carboxylic acids as additives for lubricating oil compositions is known. The said salts have a dispersant property so that they, when applied in such composition, ensure that the inside of engine cylinders remains clean and that deposition of carbonaceous products on pistons and in piston grooves is counteracted, so that piston-ring sticking is prevented.

It is also known to prepare basic (or overbased) alkaline earth metal salts of such acids. The overbasing provides an alkaline reserve which, when applied in lubricating oil compositions, reacts with and neutralizes acidic compounds formed during the operation of the engine in which the composition is applied. Hence, sludge which may arise, is maintained dispersed due to the dispersant property of the salt while acids which would enhance sludge formation are neutralized.

In British Patent Specification No. 786,167, a process for the preparation of basic salts is described in which an organic acid is reacted with an excess of an alkaline earth metal oxide or hydroxide in an oil and subsequently carbon dioxide is passed through the reaction mixture to yield basic salts. As suitable acids are mentioned substituted or unsubstituted aliphatic, cycloaliphatic and aromatic acids, comprising carboxylic acids, sulphur-containing acids, phosphoric acids, thio-acids, phenols and partial esters of sulphur- and phosphorus-containing acids.

The incorporation of basic salts into lubricating oil compositions in some cases gives rise to problems. One of these problems is that the lubricating oil compositions tend to form haze on standing. Haze may occur by a phase separation between the basic salt complexes and the base oil, which may lead to precipitation of the complexes. This problem is more pronounced now that many lubricating base oils have been subjected to hydrocracking and/or hydrotreating.

As a solution for this problem it has been proposed in GB-A-1,290,251 to add to the lubricating oil composition an aliphatic carboxylic acid or anhydride having at least 23 aliphatic carbon atoms per carboxy group. Examples of such an acid or anhydride include hydrocarbon-substituted succinic acids or anhydrides having at least 50 aliphatic carbon atoms. The latter acids and anhydrides are described in e.g. US-A-3,219,666.

It has now been found that addition of such acids or anhydrides to a basic salt-containing lubricating oil composition does not always eliminate the haze entirely. Applicants have found that when the basic salt is prepared in the presence of the aliphatic acid or anhydride, surprisingly a stable, clear solution is obtained in which no haze occurs.

SUMMARY OF THE INVENTION

Accordingly, the present invention provides a process for the preparation of a basic alkaline earth metal salt of a blend of organic carboxylic acids, which comprises
 (a) preparing a mixture of one equivalent of the blend of organic carboxylic acids and more than one equivalent of an alkaline earth metal hydroxide and/or oxide in a hydrocarbon solvent;
 (b) introducing carbon dioxide into the mixture obtained in an amount of at least 0.5 equivalent carbon dioxide per equivalent of excess alkaline earth metal; and
 (c) removing residual solids, if any, and an aqueous layer, if any, whereby
the blend of organic carboxylic acids comprises an oil-soluble alkyl salicylic acid and one or more hydrocarbon-substituted succinic acids or anhydrides in which the hydrocarbon radical has a number average molecular weight from about 120 to about 5000.

The alkyl salicyclic acid used in the process of the present invention is rendered oil-soluble by the alkyl substituent or substituents it contains. It is evident that the alkyl salicylic acid may contain more than one, e.g. two or three, alkyl substituents. Suitably the number of carbon atoms in the alkyl substituent(s) is at least four, and preferably ranges from 8 to 30. Especially when the alkyl salicylic acid—mainly—contains only one alkyl substituent the alkyl group contains most preferably from 12 to 26 carbon atoms. The alkyl group(s) may be linear or branched, but are suitably linear.

The hydrocarbon substituent in the succinic acid or anhydride preferably derived froma polyolefin. It is suitably derived from a homopolymer or copolymer of one or more olefin monomers having 2 to 16 carbon atoms, preferably from 2 to 6 carbon atoms. The copolymers include random, block and tapered copolymers. Suitable monomers include ethene, propene, butenes, isobutenes, pentenes, octenes, and also diolefines such as butadiene and isoprene. If a diene is used as monomer the resulting polymer is preferably hydrogenated to saturate at least 90%, more preferably substantially all unsaturated bonds. Conveniently the hydrocarbon substituent is a linear one derived from an ethylene polymer, or a branched one derived from a propene polymer or oligomer. It is especially preferred to use an alkenyl substituent derived from polyisobutylene.

As previously mentioned the average number of molecular weight of the hydrocarbon substituent should be from about 120 to about 5000. Preferably the number average molecular weight is from 500 to 1500.

The number average molecular weight (Mn) can easily be determined by vapour pressure osmometry or by gel permeation chromatography with calibration of the polymer, as will be appreciated by those skilled in the art. The weight average molecular weight (Mw) can also be determined by gel permeation chromatography. The quotient Mw/Mn, which is a measure indicating the width of molecular weight distribution, has usually a value from about 1.5 to about 4.0.

The average number of succinic groups per hydrocarbon group can be greater than 1. This means that then at least some hydrocarbon moieties are connected to at least two succinic groups. Preferably, the average number of succinic groups per hydrocarbon group is between about 0.5 and about 3.

The preparation of hydrocarbon-substituted succinic anhydride is known in the art. In case a polyolefin is used as substituent substituted succinic anhydride can conveniently be prepared by mixing the polyolefin, e.g. polyisobutylene, with maleic anhydride and passing chlorine through the mixture yielding hydrochloric acid and alkenyl-substituted succinic anhydride, as described in e.g. GB-A-949,981 and corresponding U.S. Pat. No. 3,231,587.

Another method for the preparation of substituted succinic anhydride is described in US-A-3,172,892, according to which a halogenated, in particular chlorinated, polyolefin is reacted with maleic anhydride.

From e.g. NL-A-7412057 and corresponding BG 1,483,729 it is known to prepare hydrocarbon-substituted succinic anhydride by reacting thermally a polyolefin with maleic anhydride. It is further possible to combine the methods of this Dutch application and GB-A-949,981 and corresponding U.S. Pat. No. 3,231,587, as is illustrated in GB-A-1,440,219 and corresponding U.S. Pat. No. 3,912,764. The products prepared in this way include compounds in which the alkenyl chain is connected to one or both of the alpha carbon atoms of the succinic group.

The ratios between the alkyl salicylic acid and the hydrocarbonsubstituted succinic acid or anhydride may vary within wide ranges. Advantageously the equivalent ratio of the alkyl salicylic acid to hydrocarbon-substituted succinic acid or anhydride ranges from about 15:1 to about 1:10, preferably from about 4:1 to about 1:1.

The alkaline earth metal salts prepared include magnesium, calcium, strontium and barium salts. Preferably, the alkaline earth metal applied is magnesium or calcium.

The reaction mixture prepared in step (a) of the present process suitably further contains a promoter, preferably an oxygen-containing organic solvent and optionally water. Suitable solvents include $C_{1-6}$ alcohols, polyhydric alcohols such as glycol, propylene glycol, glycerol or 1,3-dihydroxypropane, ethers such as $C_{1-4}$ monoethers of glycol or propylene glycol, diisopropyl ether, 1,3- or 1,4-dioxane, or 1,3-dioxolane. Preferably the promoter is a $C_{1-6}$ alcohol, in particular methanol.

It will be appreciated that in industrial processes use may be made of technical solvents, and that the use of technically pure promoters, such as methanol, might incur the presence of water. Hence, in such cases addition of water per se is not required since its addition is made implicitly by the addition of the promoter.

The preparation of the mixture according to step (a) of the present process can be carried out at any possible way, e.g. by mixing the alkaline earth metal hydroxide and/or oxide with the promoter and adding the acids, whether or not in the presence of the promoter or the hydrocarbon solvent to the resulting mixture. It is preferred to mix the blend of the acids and the alkaline earth metal hydroxide and/or oxide in a hydrocarbon solvent and subsequently adding the promoter. The promoter may contain a substantial amount of water. Preferably the water content is adjusted such that the percentage of water in the mixture amounts to 0 to 10%w, based on the total liquids.

The hydrocarbon solvent can be selected from a wide variety of solvents. Suitable solvents include hydrocarbon oils, such as solvent-refined and/or hydrogenated lubricating oils having a kinematic viscosity of 3.5–35 $mm^2/s$ at 100° C. Preferably it is an aromatic hydrocarbon fraction rich in aromatics, such as gasoline. Suitable hydrocarbon solvents are benzene, toluene, xylene or mixtures thereof, xylene being particularly preferred. The amount of the solvent is not critical. Promoter:solvent volume ratios up to about 1 can suitably be applied, preference being given to ratios in the range from about 0.1 to about 0.6.

The concentration of the organic carboxylic acid in the solvent or solvent mixture can vary within wide limits. Suitably the equivalent concentration of acids is from about 0.01 to about 1 molar equivalent/kilogram, preferably from about 0.1 to about 0.8, based on the combined weight of organic carboxylic acids and hydrocarbon solvent.

The amount of alkaline earth metal to be added in stage (a) should be at least 1 equivalent. Preferably the amount alkaline earth metal is more, so that the subsequent carbon dioxide supply results in very basic compounds. The basicity of the products prepared according to the present process can be expressed as basicity index, the basicity index (BI) being defined as the equivalents ratio of the total of alkaline earth metal to the total of organic acids. For a high BI the amount of alkaline earth metal hydroxide and/or oxide added in stage (a) is preferably from about 10 to about 25 equivalents per equivalent acid.

The temperature at which step (a) is carried out is not critical. It may be ambient temperature or elevated temperature. Suitable temperatures include from about 15° C. to about 150° C.

In stage (b) the temperature is advantageously from about 15° C. to about 150° C., preferably from about 30° C. to about 110° C. In order to obtain the elevated temperature it may be necessary to employ elevated pressures, since the desired reaction temperature may be above the atmospheric reflux temperature of the reaction mixture. Suitable pressures include 1 to 15 bar abs. Higher pressures are possible, but merely add to the costs of the process. The rate at which the carbon dioxide is introduced is advantageously from 0.05 to 1.0 equivalent carbon dioxide per equivalent acid per minute. The carbon dioxide introduction is conveniently carried out by passing carbon dioxide, or a mixture of carbon dioxide with an inert gas, such as air or nitrogen, through the reaction mixture under slightly higher pressure than the pressure prevailing in the reaction mixture. Higher pressures may be employed. Carbon dioxide will be absorbed in the reaction mixture and will react with the alkaline earth metal compounds present therein forming a basic complex salt of the organic acid salt and carbonate, hydroxide and/or oxide. The amount of carbon dioxide to be taken up in stage (b) is to a certain extent dependent on the amount of alkaline earth metal added in stage (a) of the present process. Suitably the relative amount of carbon dioxide is somewhat less than the relative amount of alkaline earth metal hydroxide or oxide.

Preferably the introduction of carbon dioxide in stage (b) is stopped after 0.5 to 0.9 equivalent carbon dioxide per equivalent alkaline earth metal has been taken up. Conveniently, this corresponds with 5 to 23 equivalent carbon dioxide per equivalent acid for high BI's mentioned above.

It has been found that an ageing period between stage (b) and stage (c) can be advantageous, since it increases the BI of the resulting basic salt. Such an ageing period amounts suitably to at least 15 min. A maximum period is generally imposed by practical and/or economical reasons, and is generally below 20 hours. Preferably the period between stages (b) and (c) is from 1 to 4 hrs.

The reaction mixture at the end of stage (b) may be worked up by any method known in the art. It may be subjected to a centrifuging treatment to remove solids comprising unreacted alkaline earth metal hydroxide and/or oxide and/or non-colloidal alkaline earth metal carbonate, if any. The resulting solution may then be subjected to a liquid-phase separation. One liquid phase can be an aqueous layer which may contain the promoter when it is used, the other one is the hydrocarbon solvent plus the basic salts dispersed therein. It is also possible to reverse the above operations.

The present process can be used for the preparation of basic salts having a wide variety of basicity indices. So, it would be possible to prepare basic salts having a relatively low BI e.g. from 1 to 10. The present process, is also suitable for preparing basic salts having a basicity index from 10 to 20.

The process described is a one-step process. However it is possible to integrate the process according to the present invention in a two-step process, in particular in a two-step process according European Pat. No. 248,465. This is particularly advantageous when basic salts with a high BI are to be prepared. Thereto, stages (a) and (b) are carried out in two stages, a1, a2, b1 and b2 respectively, whereby the stages comprise:

(a1) preparing a mixture of one equivalent of the blend of the organic carboxylic acids and more than one equivalent of an alkaline earth metal hydroxide and/or oxide in a hydrocarbon solvent;

(b1) introducing carbon dioxide into the mixture obtained until at least 0.5 equivalent carbon dioxide per equivalent of excess alkaline earth metal has been taken up;

(a2) adding at least one further equivalent of alkaline earth metal hydroxide and/or oxide to the reaction mixture, so that the total amount of alkaline earth metal hydroxide and/or oxide is at least 10 equivalent;

(b2) resuming the introduction of carbon dioxide to the resulting mixture.

Between stages (b1) and (a2) and after (b2) ageing periods can be employed as is indicated in the above patent application. The ageing period after stage (b2) corresponds with the above-mentioned ageing period between stages (b) and (c).

The process according to the present invention can be carried out batchwise and also in a continuous manner.

The basic salts are excellent detergent additives in oils. Therefore the present invention also provides oil compositions comprising a major amount of a base oil and a minor amount of a basic alkaline earth metal salt as described hereinbefore. Preferably the base oil is a lubricating base oil.

The lubricating base oil in the composition according to the invention will constitute more than 50%w of the composition. It can be selected from mineral lubricating oils of varying viscosities, but it also includes a synthetic lubricant, such as ester-type lubricant or a polyolefin-type fluid, or a vegetable oil, or a grease.

Fuel compositions which are used in marine diesel engines usually contain some sulphur compounds. To neutralize the acidic compounds formed from these sulphur compounds a relatively high concentration of the basic salt is employed. Preferably, these marine lubricating oil compositions contain from about 5 to about 30%w of basic alkaline earth metal salt. Lubricating oil compositions for road engines may contain lower concentrations. The amount of basic alkaline earth metal salt in these lubricating oil compositions is preferably from 0.01 to 5%w, in particular from 0.1 to 4.0%w.

Fuels, such as gasoline, kerosine, diesel fuel and gas oils, can also contain the above basic salts. The amount of these salts is similar to that in road engine lubricating oil compositions or lower; conveniently the amount is from 0.001 to 5%w, in particular from 0.01 to 1.0%w.

The lubricating oil composition can be prepared by mixing a concentrate containing up to 60%w of a basic salt as described above in a lubricating oil, with a lubricating base oil to give the desired concentration. Such a concentrate is conveniently prepared by addition of a lubricating oil to the product obtained after completion of stage (c), and removal of any volatile hydrocarbon solvent, water and alcohol, if present. The lubricating oil may be the same as the one indicated above as a suitable hydrocarbon solvent. The concentrate may conveniently contain a stabiliser, which is selected from a variety of organic compounds, such as those described in British patent specification No. 818,325. These compounds include mono- or polyhydric alcohols, alkyl amines and alkyl phenols.

The lubricating oil compositions may further contain a number of other additives, such as antioxidants, foam inhibitors, corrosion inhibitors, viscosity index improvers, and pour point depressants as can be established by a person skilled in the art.

The invention will be illustrated by means of the following Examples.

EXAMPLE I

A mixture of 225 g of a 60%w solution of $C_{14-18}$ alkyl salicylic acid (ASA) in xylene (0.297 eq) and 51 g polyisobutenyl-substituted succinic acid (PSA) (0.099 eq) in which the polyisobutenyl radical had a number average molecular weight of 1000, was introduced in 714 g xylene. To this mixture 278 g calcium hydroxide was added resulting in an equivalent ratio of 19 eq Ca(OH)$_2$/eq acid. To this mixture 166 g methanol containing 3%w of water, was added. The mixture was heated to the reaction temperature, 85° C., and stirred for 1 h, during which neutralization took place. Subsequently carbon dioxide was introduced at a rate of 0.12 eq $CO_2$/eg acid/min. After an uptake of 13 eq $CO_2$/eq acid the $CO_2$ introduction was stopped. The reaction mixture was subjected to an ageing period of 16 h at a temperature of 58° C. under stirring. Subsequently, the reaction mixture was allowed to settle, yielding two liquid phases and the methanol-water layer formed was separated. From the xylene layer residual solids were removed by centrifugation. The basicity index of the salt in the xylene layer, determined by acidimetric titration, was 14.5.

195.6 g of the product obtained was introduced into 300 g of a hydrotreated mineral lubricating oil, the mixture obtained was subjected to vacuum distillation to remove xylene, yielding a composition containing 10.0%m calcium.

EXAMPLE II

This example illustrates the process according to the present invention carried out in a continuous manner. ASA, PSA and Ca(OH)$_2$ in an equivalent ratio of 0.75:0.25:19, in a methanol/xylene solution were continuously fed via a neutralization vessel into a carbonation vessel. The concentration of the acids and the calcium hydroxide in the liquid phase was 0.4 eq/kg, and 7.6 eq/kg respectively. The xylene/methanol (which contained 3%w of water) ratio was 4.33. The average residence time of the mixture in the neutralization and carbonation vessels were 100 minutes. Into the carbonation vessel $CO_2$ was introduced at a rate of 0.12 eq $CO_2$/eq acid per minute and at a temperature of 100° C. Reaction product was withdrawn from the carbonation vessel such that the overall composition remained the same.

Samples were drawn from the reaction product periodically, and taken up in an oil composition as described in Example I. Sample 1 was drawn after 4 hours, and sample 2 after 7 hours. They were taken up into a lubricating oil in analogy to the method described in Example I. Sample 3, drawn at the same time as sample 2 was subjected to an ageing period of 18 h at 55° C. under stirring before being taken up in an oil composition. The BI's of the salts were 12.0 (sample 1), 16.4 (sample 2) and 17.6 (sample 3) and the calcium contents 11.5, 13.7 and 15.0%m, respectively.

EXAMPLE III

Formation of haze and/or deposits in the compositions

To assess the formation of haze and/or deposits the products were diluted with a mixture of hydrotreated lubricating oils, such that the total base number of the resulting solution was 70 mg KOH/g. The resulting solutions were stored in tubes at ambient temperature and after 2 and 7 days they were visually assessed on amount of deposits and on brightness. The amount of deposits were expressed in % by volume. The brightness was classified as "bright" (B), "slightly hazy" (sH), "hazy" (H) and "muddy" (M). By "muddy" is understood the situation that the whole test tube is cloudy and that no visual assessment of the amount of deposits is possible.

The results of the measurements are shown in the Table I below.

TABLE I

| Product of Example | BI | Stability (% vol deposits/brightness) ambient temperature | |
|---|---|---|---|
| | | 2 d | 7 d |
| I | 14.7 | 0/B | 0/B |
| II, sample 1 | 12.0 | 0/B | 0/B |
| II, sample 2 | 16.4 | 0/B | 0/B |
| II, sample 3 | 17.6 | 0/sH | 0/sH |

Comparative Experiment

An experiment similar to Example II was carried out, but using only ASA. Samples were drawn after 4 and 7 h and at 7 h with an ageing period. The samples were taken up in lubricating oil, and subjected to the same tests as described in Example III.

Results of the tests and some data of the samples are shown in Table II.

TABLE II

| Sample | After time h | BI | Stability (% vol deposits/brightness) ambient temperature | |
|---|---|---|---|---|
| | | | 2d | 7d |
| 1a | 4 | 13.7 | M | M |
| 2a | 7 | 15.5 | M | M |
| 3a | 7 + ageing period | 16.1 | M | M |

To samples 1a, 2a and 3a, diluted with lubricating oil to a Ca content of 10%w, 6%w polyisobutenyl-substituted succinic acid was added, thereby lowering the BI. The molecular weight of the polyisobutenyl substituent was about 1000. The BI and the results of the stability tests are indicated in Table III.

TABLE III

| Sample | PSA %w | Ratio ASA/PSA | BI | Stability (% vol deposits/brightness) ambient temperature | |
|---|---|---|---|---|---|
| | | | | 2d | 7d |
| 1a | 6 | 5.24 | 11.5 | 0/H | 0/H |
| 2a | 6 | 4.63 | 12.8 | M | M |
| 3a | 6 | 4.46 | 13.2 | M | M |

Though the addition of PSA improves the stability to some extent, the overall results are still unsatisfactory.

What is claimed is:

1. A process for the preparation of a basic alkaline earth metal salt of a blend of organic carboxylic acids, which comprises
    (a) preparing a mixture of one equivalent of the blend of organic carboxylic acids and more than one equivalent of an alkaline earth metal compound selected from the group consisting of hydroxides, oxides and mixtures thereof in a hydrocarbon solvent;
    (b) introducing carbon dioxide into the mixture obtained in an amount of at least 0.5 equivalent carbon dioxide per equivalent of excess alkaline earth metal; and
    (c) removing residual solids, if any, and an aqueous layer, if any, wherein the blend of organic carboxylic acids comprises an oil-soluble alkyl salicylic acid and one or more hydrocarbon-substituted succinic acids or anhydrides in which the hydrocarbon radical has a number average molecular weight from 120 to 5000.

2. The process according to claim 1, in which the alkyl salicylic acid has 12 to 26 carbon atoms in the alkyl group.

3. The process according to claim 1 or 2, in which the hydrocarbon substituent in the succinic acid or anhydride is derived from a polyolefin.

4. The process according to claim 3 in which the number average molecular weight of the hydrocarbon substituent is from 500 to 1500.

5. The process according to claim 1 or 2, in which the equivalent ratio of the alkyl salicylic acid to the hydrocarbon-substituted succinic acid or anhydride ranges from 15:1 to 1:10.

6. The process according to claim 1 or 2, in which the alkaline earth metal is magnesium or calcium.

7. The process according to claim 1 or 2, in which the mixture in stage (a) further comprises an oxygen-containing organic solvent, or mixtures thereof with water.

8. The process according to claim 7, in which the oxygen-containing solvent is a $C_{1-6}$ alcohol.

9. The process according to claim 1 or 2, in which the mixture of the blend of the organic carboxylic acids and alkaline earth metal compound oxide is prepared by mixing the acids and the alkaline earth metal compound oxide in the hydrocarbon solvent.

10. The process according to claim 1 or 2, in which the hydrocarbon solvent is selected from benzene, toluene, xylene, and a mixture thereof.

11. The process according to claim 1 or 2, in which the amount of alkaline earth metal hydroxide compound oxide added in stage (a) is from 10 to 25 equivalents per equivalent acid.

12. The process according to claim 1 or 2, in which the introduction of carbon dioxide in stage (b) is carried out at a temperature from 15° to 150° C.

13. The process according to claim 12, in which the temperature is from 30° to 110° C.

14. The process according to claim 1 or 2, in which the introduction of carbon dioxide in stage (b) is carried out at a rate of 0.5 to 1.0 equivalent carbon dioxide per equivalent acid per minute.

15. The process according to claim 1 or 2, in which carbon dioxide is introduced in stage (b) in an amount of 0.5 to 0.9 equivalent carbon dioxide per equivalent alkaline earth metal.

16. The process according to claim 1 or 2, in which the period between stages (b) and (c) is from 0.25 to 20 hours.

17. The process according to claim 1 or 2, in which stages (a) and (b) are carried out in two stages, wherein the stages comprise:
(a1) preparing a mixture of one equivalent of the blend of organic carboxylic acids and more than one equivalent of an alkaline earth metal compound selected from the group consisting of hydroxides, oxides and mixtures thereof in a hydrocarbon solvent;
(b1) introducing carbon dioxide into the mixture obtained until at least 0.5 equivalent carbon dioxide per equivalent of excess alkaline earth metal has been taken up;
(a2) adding at least one further equivalent of alkaline earth metal compound to the reaction mixture, so that the total amount of alkaline earth metal compound is at least 10 equivalent;
(b2) resuming the introduction of carbon dioxide to the resulting mixture until at least 0.5 equivalent carbon dioxide per equivalent of excess alkaline earth metal has been taken up.

18. A basic alkaline earth metal salt of a blend of organic carboxylic acids prepared according to claim 1 or 2.

19. An oil composition comprising a major amount of a base oil and a minor effective amount of a basic alkaline earth metal salt according to claim 18.

* * * * *